US009119589B2

(12) United States Patent
Zou

(10) Patent No.: US 9,119,589 B2
(45) Date of Patent: Sep. 1, 2015

(54) METHOD AND SYSTEM FOR SPECTRAL COMPUTED TOMOGRAPHY (CT) WITH SPARSE PHOTON COUNTING DETECTORS

(75) Inventor: Yu Zou, Naperville, IL (US)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 403 days.

(21) Appl. No.: 13/426,903

(22) Filed: Mar. 22, 2012

(65) Prior Publication Data
US 2013/0251097 A1 Sep. 26, 2013

(51) Int. Cl.
A61B 6/03 (2006.01)
A61B 6/00 (2006.01)

(52) U.S. Cl.
CPC ............. A61B 6/482 (2013.01); A61B 6/032 (2013.01); A61B 6/4241 (2013.01); A61B 6/4266 (2013.01)

(58) Field of Classification Search
CPC ...... A61B 6/032; A61B 6/482; A61B 6/4241; A61B 6/4266
USPC ........................................................ 378/9, 19
See application file for complete search history.

(56) References Cited

U.S. PATENT DOCUMENTS

| 4,149,249 A * | 4/1979 | Pavkovich | 378/14 |
| 4,284,895 A * | 8/1981 | Morgan et al. | 378/9 |
| 2005/0226364 A1* | 10/2005 | De Man et al. | 378/9 |
| 2006/0023835 A1* | 2/2006 | Seppi | 378/57 |
| 2007/0147574 A1* | 6/2007 | De Man et al. | 378/4 |
| 2007/0205367 A1* | 9/2007 | Deman et al. | 378/19 |
| 2007/0206721 A1* | 9/2007 | Tkaczyk et al. | 378/19 |
| 2008/0118024 A1* | 5/2008 | Cho et al. | 378/13 |
| 2009/0161816 A1* | 6/2009 | De Man et al. | 378/9 |
| 2010/0215142 A1* | 8/2010 | Dafni et al. | 378/19 |

OTHER PUBLICATIONS

Thomas G. Flohr et al., "First performance evaluation of a dual-source CT (DSCT) system", Eur Radiol (2006), 16: pp. 256-268.
Raz Carmi et al., "Material Separation with Dual-Layer CT", Nuclear Science Symposium Conference Record, Oct. 23-29, 2005, IEEE, vol. 4, pp. 1876-1878.
Yu Zou et al., "Analysis of Fast kV-switching in Dual Energy CT using a Pre-reconstruction Decomposition Technique", Medical Imaging, 2008: Physics of Medical Imaging, SPIE, vol. 6913, (2008), pp. 691313-1 through 691313-12.
J.P. Schlomka et al., "Experimental feasibility of multi-energy photon-counting K-edge imaging in pre-clinical computed tomography", Phys. Md. Biol. 53 (2008), pp. 4031-4047.

* cited by examiner

Primary Examiner — Glen Kao
(74) Attorney, Agent, or Firm — Yoshida & Associates, LLC

(57) ABSTRACT

Photon counting detectors are sparsely placed at predetermined positions in the fourth-generation geometry around an object to be scanned in spectral Computer Tomography (CT). Optionally, integrating detectors are placed between the two adjacent ones of the sparsely placed photon counting detectors in the fourth-generation geometry. Furthermore, the integrating detectors are placed in the third-generation in combination to the sparsely placed photon counting detectors at predetermined positions in the fourth-generation geometry.

16 Claims, 14 Drawing Sheets

103A

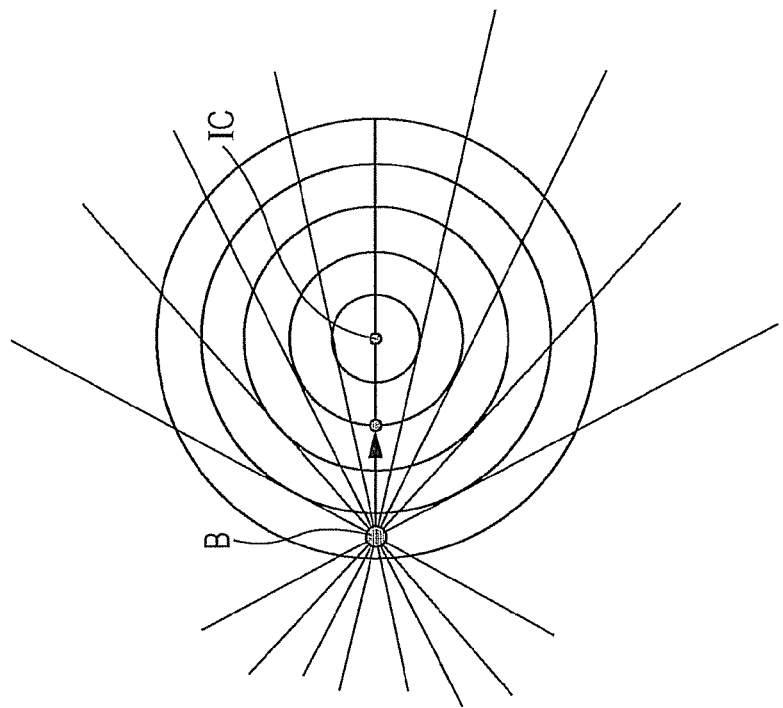
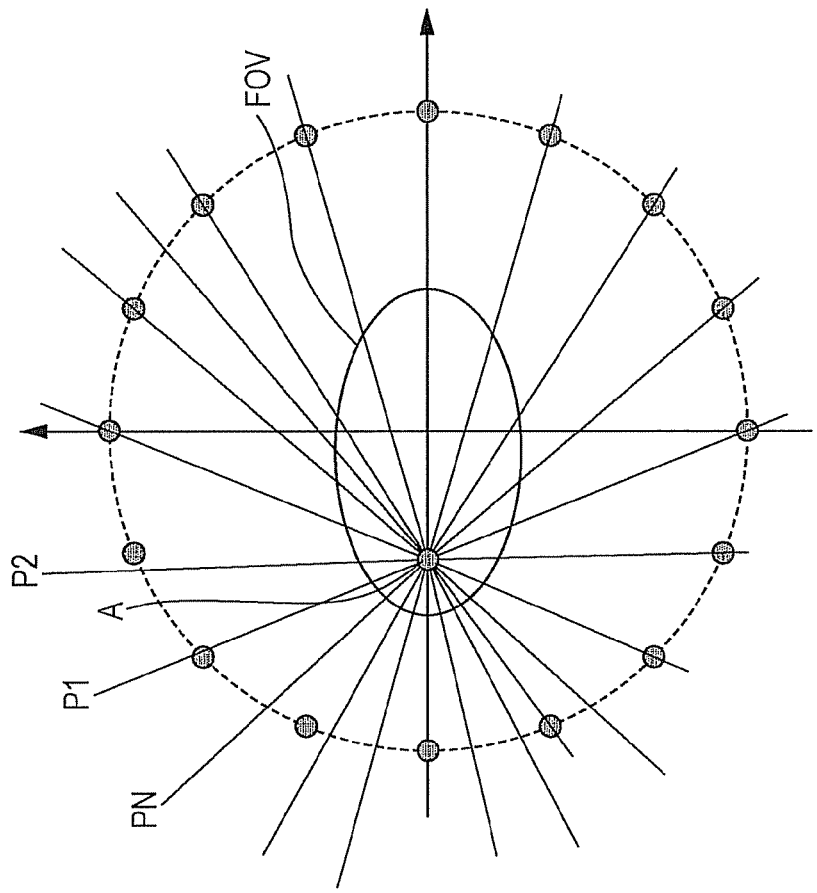

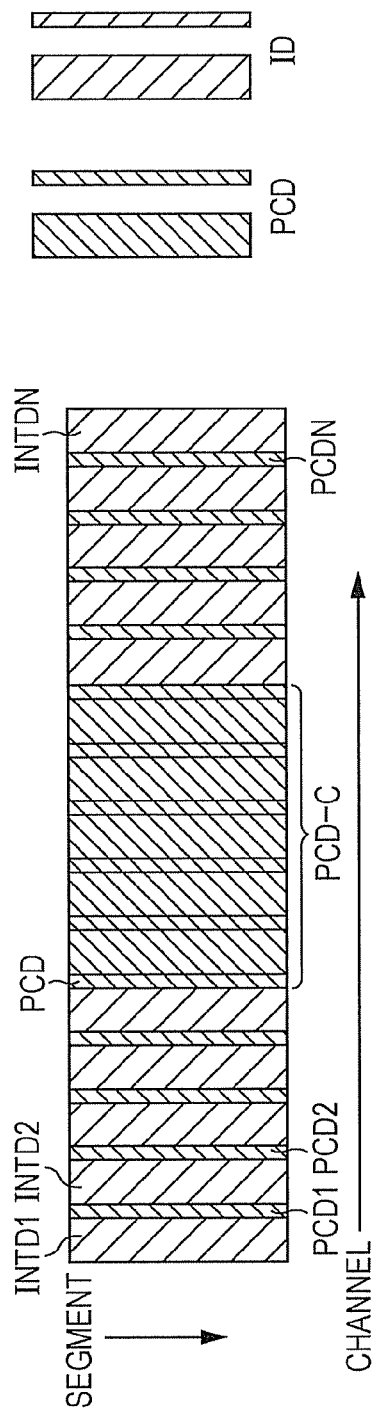
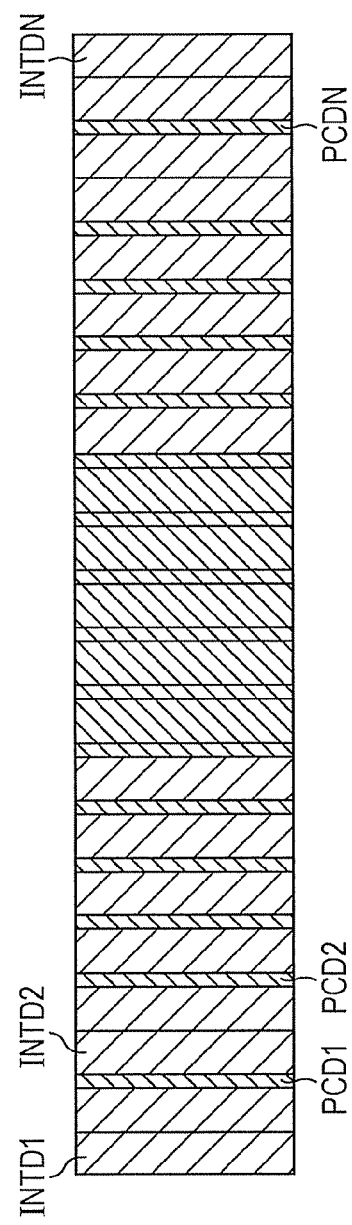
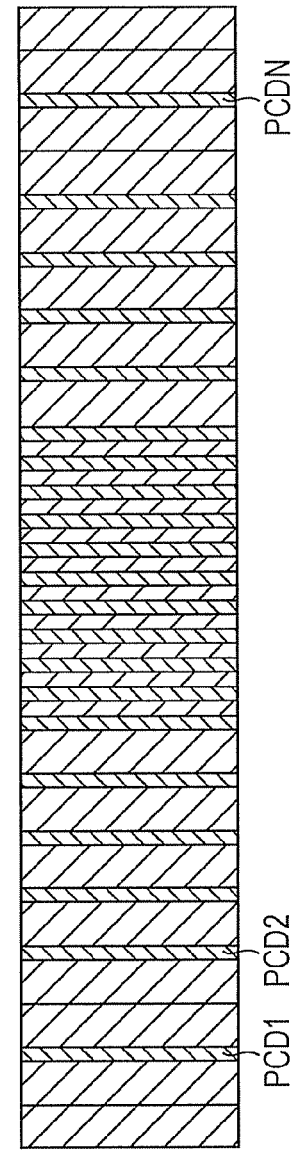
FIG. 11A
FIG. 11B
FIG. 11C

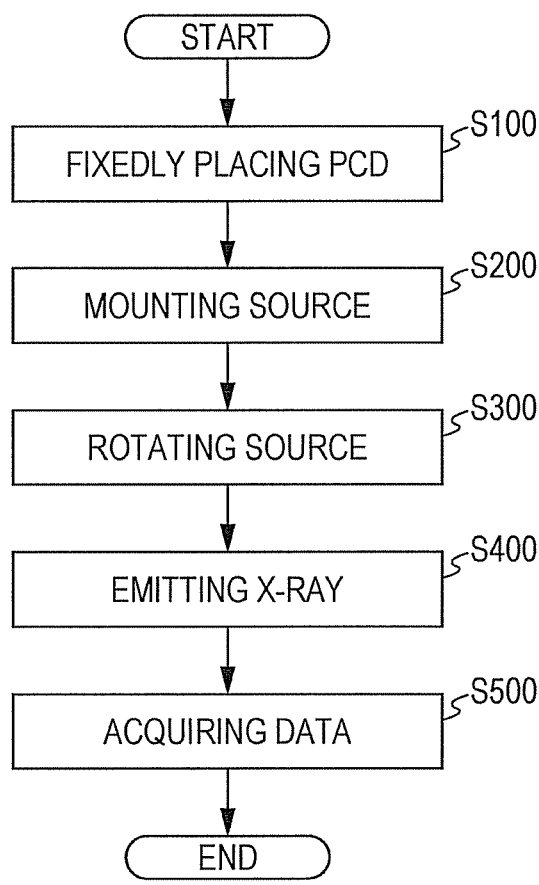

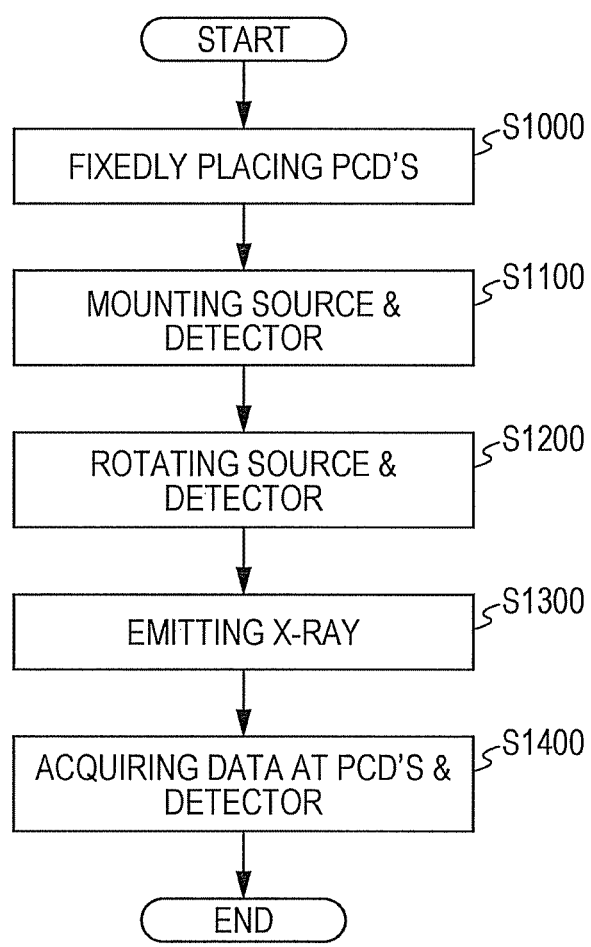

METHOD AND SYSTEM FOR SPECTRAL COMPUTED TOMOGRAPHY (CT) WITH SPARSE PHOTON COUNTING DETECTORS

FIELD OF THE INVENTION

The current invention is generally related to an image processing and system, and more particularly related to sparse photon counting detectors in spectral Computer Tomography (CT).

BACKGROUND OF THE INVENTION

The x-ray beam in most computer tomography (CT) scanners is generally polychromatic. Yet, most of the currently used CT scanners generate images based upon data according to the energy integration nature of the detectors. These conventional detectors are called energy integrating detectors for acquiring energy integration X-ray data. On the other hand, photon counting detectors are configured to acquire the spectral nature of the x-ray source rather than the energy integration nature in acquiring data. To obtain the spectral nature of the transmitted X-ray data, the photo counting detectors split the x-ray beam into its component energies or spectrum bins and counts a number of photons in each of the bins. The use of the spectral nature of the x-ray source in CT is often referred to as spectral CT. Since spectral CT involves the detection of transmitted X-ray at two or more energy levels, spectral CT generally includes dual-energy CT by definition.

Spectral CT is advantageous over conventional CT. Spectral CT offers the additional clinical information inherent in the full spectrum of an x-ray beam. For example, spectral CT facilitates in discriminating tissues, differentiating between materials such as tissues containing calcium and iodine or enhancing the detection of smaller vessels. Among other advantages, spectral CT is also expected to reduce beam hardening artifacts. Spectral CT is also expected to increase accuracy in CT numbers independent of scanners.

Prior art attempts included the use of the conventional integrating detectors in implementing spectral CT. One attempt included dual sources and dual integrating detector units that are placed on the gantry at the predetermined angle with each other for acquiring the data as the gantry rotates around a patient. Another attempt included a single source that performs kV-switching and a single integrating detector unit that are placed on the gantry for acquiring the data as the gantry rotates around a patient. Yet another attempt included a single source and dual integrating detector units that are layered on the gantry for acquiring the data as the gantry rotates around a patient. All of these prior art attempts for spectral CT are not successful in substantially solving issues such as beam hardening, temporal resolution, noise, poor detector response, poor energy separation and so on for reconstructing clinically viable images.

Prior art has also attempted to replace the conventional integrating detectors by the photon counting detectors in implementing spectral CT. In general, photon counting detectors are costly and have a predetermined response rate. Although at least one experimental spectral CT system has been reported, the costs of high-rate photon counting detectors are prohibitive for a full-scale implementation. Despite some advancement in the photon counting detector technology, the currently available photon counting detectors still require solutions to implementation issues such as pile-up effects, scatter effects, spatial resolution, temporal resolution and dose efficiency. For the above reasons, it is still desired to invent spectral CT systems for improving the use of the photon counting detectors in view of the above issues.

BRIEF DESCRIPTION OF THE DRAWINGS

FIG. 10A is a diagram illustrating the relationship among the source positions, the field of view (FOV) and an arbitrary image point in the FOV in sparse view sampling.

FIG. 10B is a diagram illustrating a sparsity level of the detectors in accordance with the radius in sparse detector sampling.

FIG. 11A is a diagram depicting one non-equidistant configuration pattern of the photon counting detectors (PCD) and the integrating counters (ITGD) in a certain embodiment of the hybrid detector in the CT scanner system according to the current invention.

FIG. 11B is a diagram depicting a second non-equidistant configuration pattern of the photon counting detectors (PCD) and the integrating counters (ITGD) in a certain embodiment of the hybrid detector in the CT scanner system according to the current invention.

FIG. 11C is a diagram depicting a third non-equidistant configuration pattern of the photon counting detectors (PCD) and the integrating counters (ITGD) in a certain embodiment of the hybrid detector in the CT scanner system according to the current invention.

FIG. 13 is a flow chart illustrating steps or acts involved in a process or method of acquiring data for spectral CT using sparse photon counting detectors according to the current invention.

FIG. 14 is a flow chart illustrating steps or acts involved in a process or method of acquiring data for spectral CT using a combination of sparse photon counting detectors and integrating detectors according to the current invention.

DETAILED DESCRIPTION OF THE EMBODIMENT(S)

Figure 1:
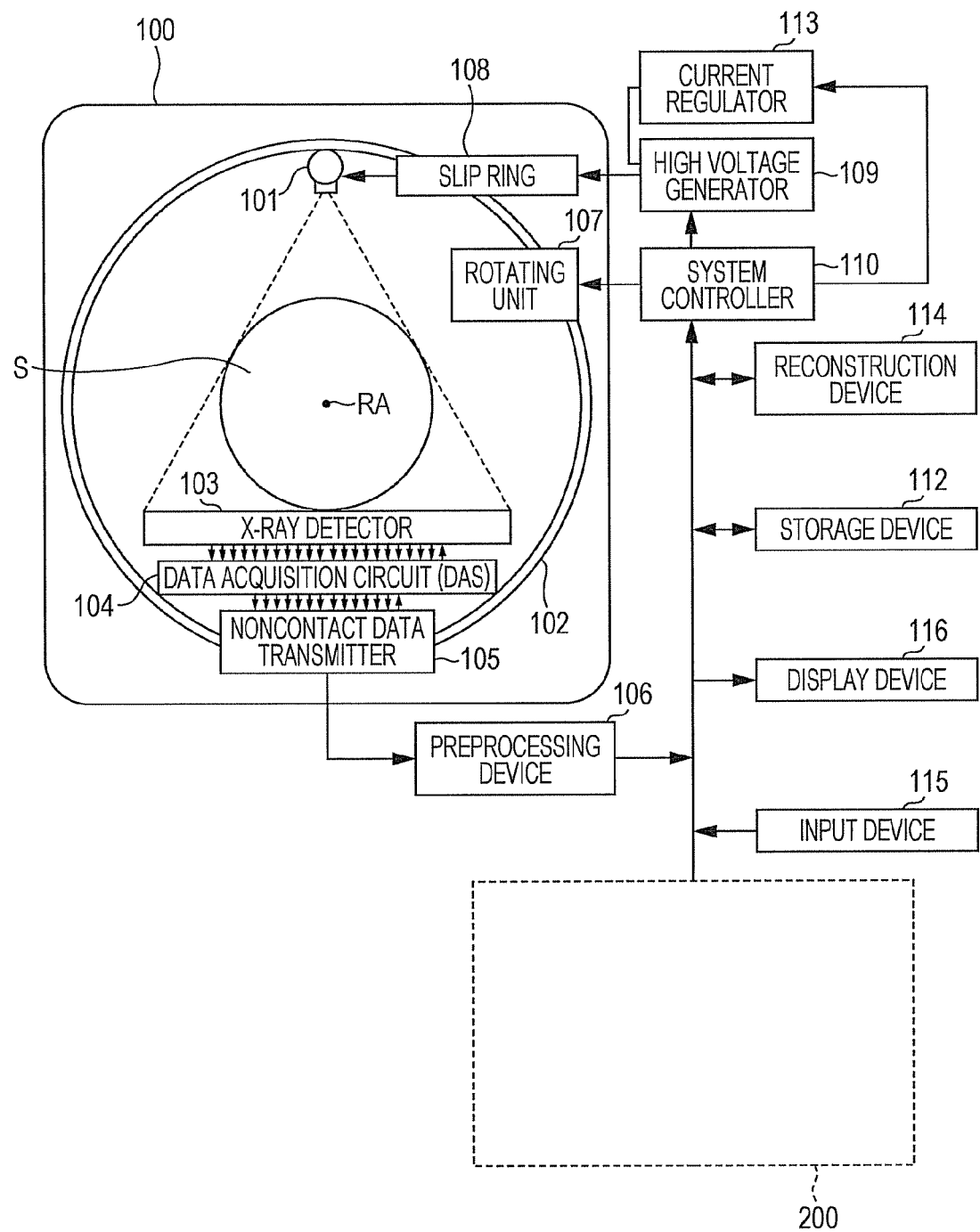
FIG. 1 is a diagram illustrating one prior art X-ray CT apparatus or scanner according to the current invention including a gantry and other devices or units.

Referring now to the drawings, wherein like reference numerals designate corresponding structures throughout the views, and referring in particular to FIG. 1, a diagram illustrates one prior art X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S. The X-ray detector 103 further includes individual detector elements or units that are conventional integrating detectors.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116 and the scan plan support apparatus 200. The scan plan support apparatus 200 includes a function for supporting an imaging technician to develop a scan plan.

The detectors are either rotated or fixed with respect to the patient among various generations of the CT scanner systems. The above described prior art CT system is one example of a third-generation geometry in which the X-ray tube 101 and the X-ray detector 103 are diametrically mounted on the annular frame 102 and are rotated around the subject S as the annular frame 102 is rotated about the rotation axis RA. On the other hand, a fourth-generation geometry has detectors that are fixedly placed around the patient and a X-ray tube that rotates around the patient.

Figure 2:
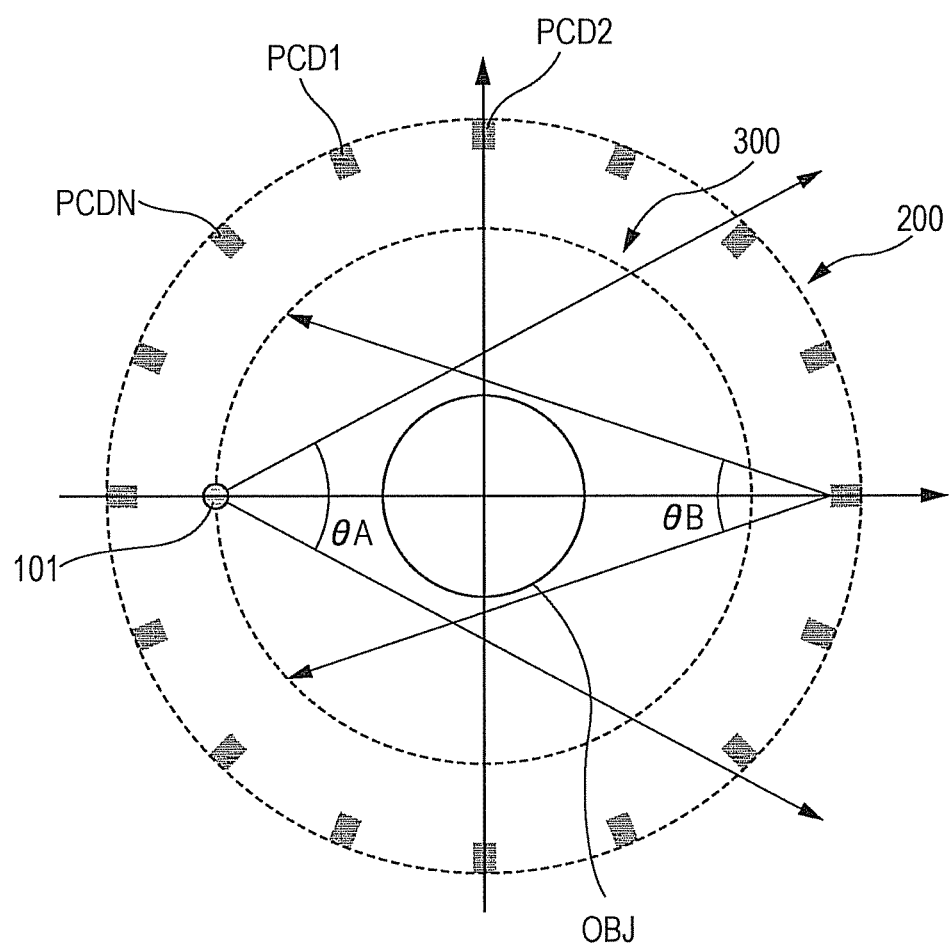
FIG. 2 is a diagram illustrating one embodiment for placing the photon counting detectors (PCD) in a predetermined fourth-generation geometry in the CT scanner system according to the current invention.

Now referring to FIG. 2, a diagram illustrates one embodiment for placing the photon counting detectors (PCD) in a predetermined fourth-generation geometry in the CT scanner system according to the current invention. The diagram merely illustrates a relative relationship among an object OBJ to be scanned, an X-ray source 101 and the photon counting detectors PCD1 through PCDN in one exemplary embodiment. For the sake of simplicity, the diagram excludes other components and units that are necessary in acquiring and processing data as well as reconstructing an image based upon the acquired data. In general, the photon counting detectors PCD1 through PCDN are each a commercially available device and output a photon count for each of predetermined energy components. Although approximately one hundred to three hundred photon counting detectors are utilized in certain embodiments, the above numerical range of the photon counting detectors is merely exemplary, and the claimed invention is not necessarily limited to any particular number of the photon counting detectors.

Still referring to FIG. 2, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition. On the other hand, the X-ray source 101 is mounted on a rotating portion 300 such as the annular frame 102 in the gantry 100 so that the X-ray source 101 projects X-ray with a predetermined source fan beam angle θA towards the object OBJ while the X-ray source 101 rotates around the object OBJ inside the sparsely placed photon counting detectors PCD1 through PCDN. Consequently, the photon counting detectors PCD1 through PCDN individually detect with a predetermined detector fan beam angle θB the X-ray that has been transmitted through the object OBJ and output a number of photons for each of predetermined energy components.

In the above embodiment, the photon counting detectors (PCD) are sparsely and fixedly placed along a first circular path around the object OBJ while at least one X-ray source 101 rotates along a second circular path around the object OBJ. Furthermore, the above embodiment illustrates that the first circular path is larger and outside the second circular path around the object OBJ. Although it is not illustrated in a drawing, an alternative embodiment optionally reverses the relative relation of the first and second circular paths so that the second circular path for the X-ray source 101 is larger and outside the first circular path of the sparsely placed photon counting detectors PCD1 through PCDN around the object OBJ to practice the current invention.

There are other alternative embodiments for placing the photon counting detectors (PCD) in a predetermined fourth-generation geometry in the CT scanner system according to the current invention. Again, although it is not illustrated in a drawing, a second alternative embodiment optionally includes more than one X-ray source 101, and a plurality of the X-ray sources 101 is mounted on the rotating portion 300 such as the annular frame 102 at a predetermined angle with each other. At least one of the X-ray sources 101 is optionally a single energy source in certain embodiments. By the same token, a third alternative embodiment optionally includes the X-ray source 101, which is configured to perform a kV-switching function for emitting X-ray at a predetermined high-level energy and a predetermined low-level energy.

Figure 3:
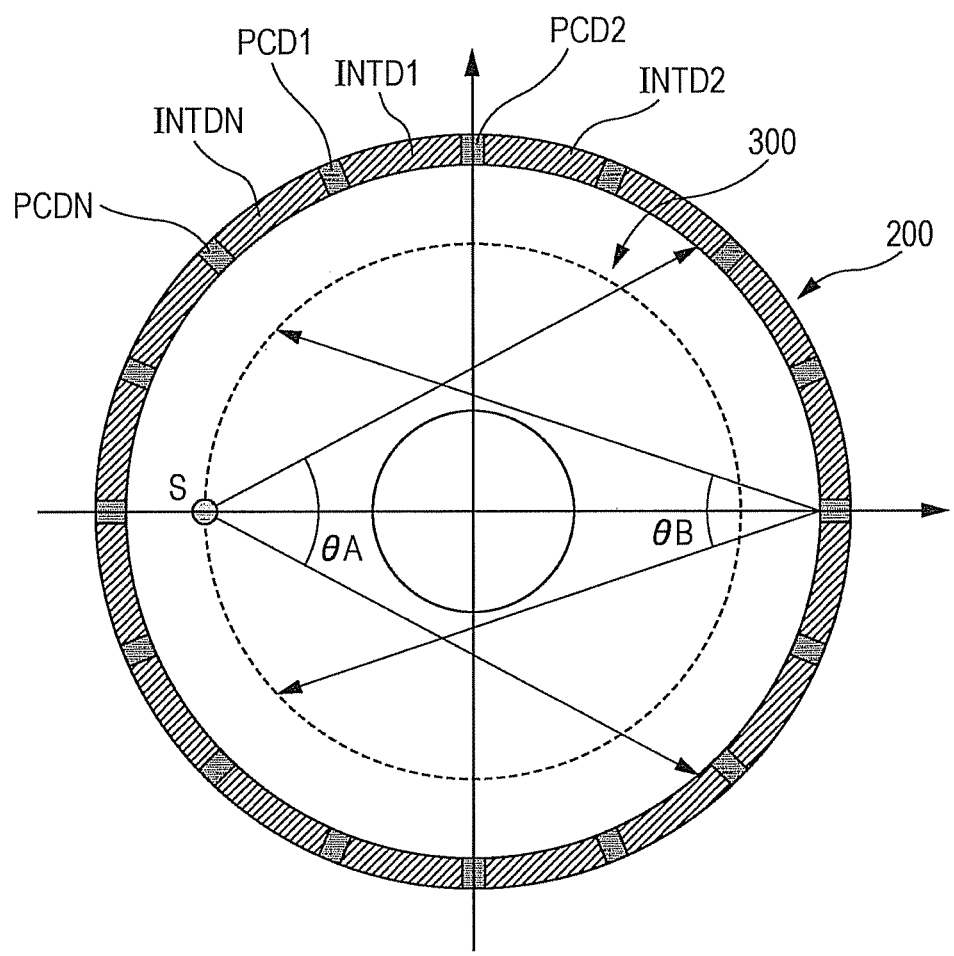
FIG. 3 is a diagram illustrating one embodiment for placing a hybrid detector in a predetermined fourth-generation geometry in the CT scanner system according to the current invention.

Now referring to FIG. 3, a diagram illustrates one embodiment for placing a hybrid detector in a predetermined fourth-generation geometry in the CT scanner system according to the current invention. One exemplary hybrid detector includes both the photon counting detectors (PCD) and integrating detectors (INTD). The diagram merely illustrates a relative relationship among an object OBJ to be scanned, an X-ray source 101, the photon counting detectors PCD1 through PCDN and the integrating detectors INTD1 through INTDN in one exemplary embodiment. For the sake of simplicity, the diagram excludes other components and units that are necessary in acquiring and processing data as well as reconstructing an image based upon the acquired data. In general, the photon counting detectors PCD1 through PCDN are each a commercially available device and output a photon count for each of predetermined energy components. Although approximately one hundred to three hundred photon counting detectors are utilized in certain embodiments, the above numerical range of the photon counting detectors is merely exemplary, and the claimed invention is not necessarily limited to any particular number of the photon counting detectors. By the same token, the integrating detectors INTD1 through INTDN are also each a commercially available device and output a single integration value for all of the energy components. Although a corresponding number of approximately one hundred to three hundred integrating detectors is utilized in certain embodiments, the above numerical range of the integrating detectors is merely exemplary, and the claimed invention is not necessarily limited to any particular number of the integrating detectors.

Still referring to FIG. 3, one embodiment includes a predetermined number of the photon counting detectors (PCD) and the integrating detectors (INTD), both of which are placed in a predetermined fourth-generation geometry in the CT scanner system according to the current invention. The photon counting detectors (PCD) are sparsely placed around the object OBJ in a predetermined geometry such as a circle at certain positions along the circumference. The embodiment further includes the integrating detectors (INTD), which are placed between adjacent the photon counting detectors (PCD). For example, the integrating detector INTD1 is fixedly placed between the two adjacent photon counting detectors PCD1 and PCD2 on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition.

The above describe embodiment further includes the X-ray source 101, which is mounted on a rotating portion 300 such as the annular frame 102 in the gantry 100. As the annular frame 102 rotates during the data acquisition, the X-ray source 101 projects X-ray with a predetermined source fan beam angle θA towards the object OBJ while the X-ray source 101 rotates around the object OBJ inside the sparsely placed photon counting detectors PCD1 through PCDN and the integrating detectors INTD1 through INTDN. Consequently, the photon counting detectors PCD1 through PCDN individually detect with a predetermined detector fan beam angle the X-ray that has been transmitted through the object OBJ and output a number of photons for each of predetermined energy components. At the same time, the integrating detectors INTD1 through INTDN also individually detect the X-ray that has been transmitted through the object OBJ and output a single value. Thus, the above describe exemplary embodiment acquires two sets of projection data from the two kinds of detectors.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique. The integrating detectors INTD1 through INTDN also acquire a second set of projection data, and the projection data from the integrating detectors INTD1 through INTDN is used to generally improve image quality. In acquiring the projection data, a sampling on the source trajectory is optionally made dense in order to enhance spatial resolution. On the other hand, software correction is optionally needed to reduce scatter in the acquired data as no anti-scatter gird is used in the channel direction on the hybrid detector.

In the above embodiment, the photon counting detectors (PCD) and the integrating detectors (INTD) are fixedly placed along a first circular path around the object OBJ while at least one X-ray source 101 rotates along a second circular path around the same object OBJ. Furthermore, the above embodiment illustrates that the first circular path is larger and outside the second circular path around the object OBJ. Although it is not illustrated in a drawing, an alternative embodiment optionally reverses the relative relation of the first and second circular paths so that the second circular path for the X-ray source 101 is larger and outside the first circular path of the sparsely placed photon counting detectors PCD1 through PCDN and the integrating detectors INTD1 through INTDN around the object OBJ to practice the current invention.

Figure 4:
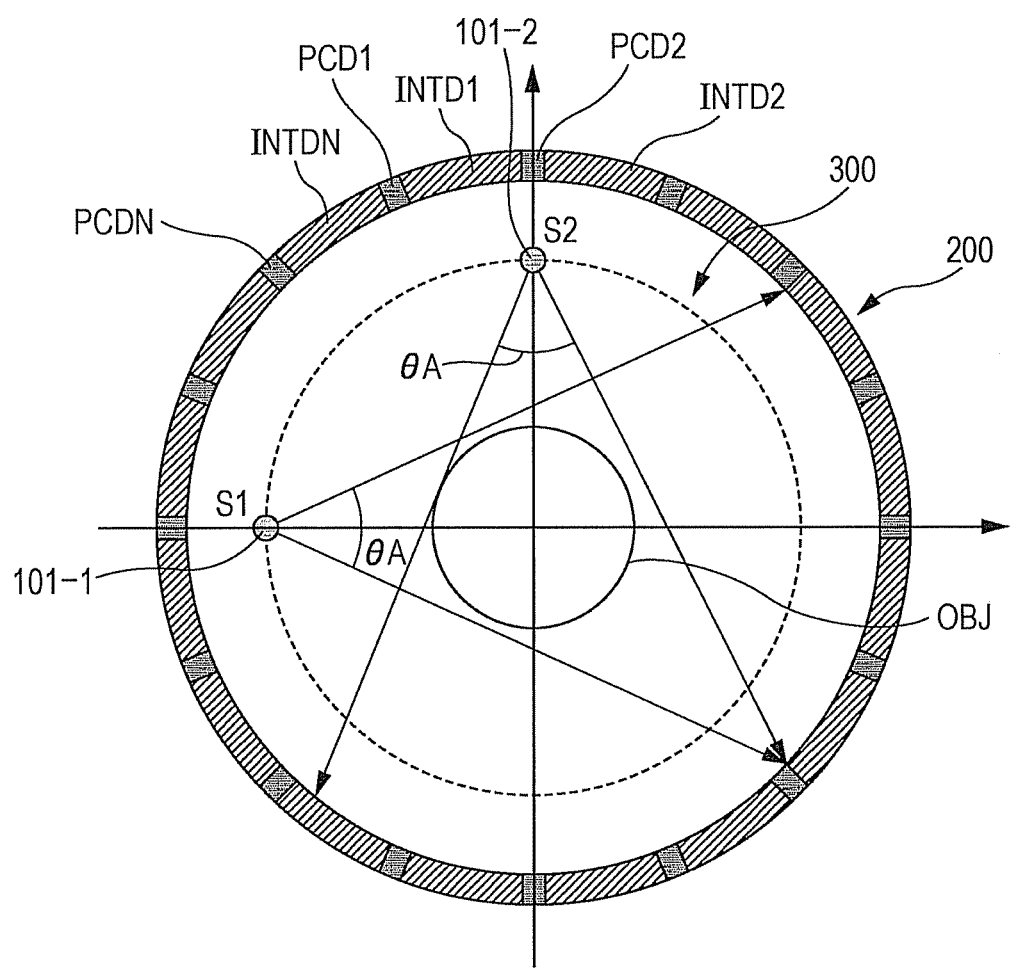
FIG. 4 is a diagram illustrating a second alternative embodiment including more than one X-ray source 101 and a hybrid detector in a predetermined fourth-generation geometry in the CT scanner system according to the current invention.

Now referring to FIG. 4, a diagram illustrates a second alternative embodiment including more than one X-ray source 101 and a hybrid detector in a predetermined fourth-generation geometry in the CT scanner system according to the current invention. One exemplary hybrid detector includes both the photon counting detectors (PCD) and integrating detectors (INTD) as described with respect to FIG. 3. The diagram merely illustrates a relative relationship among an object OBJ to be scanned, a pair of the X-ray sources 101-1, 101-2, the photon counting detectors PCD1 through PCDN and the integrating detectors INTD1 through INTDN in one exemplary embodiment. For the sake of simplicity, the diagram excludes other components and units that are necessary in acquiring and processing data as well as reconstructing an image based upon the acquired data. The alternative embodiment optionally includes that a pair of the X-ray sources 101-1 and 101-2 is mounted at predetermined locations such as S1 and S2 on the rotating portion 300 such as the annular frame 102 at a predetermined angle with each other. With respect to FIG. 4, certain other components and units may not be further described since they are substantially identical to those that are indicated by the same reference numerals and symbols in FIG. 2 or 3.

The two X-ray sources 101-1 and 101-2 are respectively mounted at the locations S1 and S2 on the rotating portion 300 such as the annular frame 102 in the gantry 100 and simultaneously rotate around the object OBJ about the same center. Although the angle between the positions S1 and S2 on the rotating portion 300 is approximately 90 degrees in one exemplary alternative embodiment, the angle is not necessarily limited to a particular angle. As the rotating portion 300 rotates during the data acquisition, the X-ray sources 101-1 and 101-2 each project X-ray with a predetermined source fan beam angle θA towards the object OBJ while the X-ray sources 101-1 and 101-2 rotate around the object OBJ inside the sparsely placed photon counting detectors PCD1 through PCDN and the integrating detectors INTD1 through INTDN. Consequently, the photon counting detectors PCD1 through PCDN individually detect with a predetermined detector fan beam angle θB the X-ray that has been transmitted through the object OBJ and output a number of photons for each of predetermined energy components. At the same time, the integrating detectors INTD1 through INTDN also individually detect the X-ray that has been transmitted through the object OBJ and output a single value. Since the two X-ray sources 101-1 and 101-2 simultaneously emit X-ray towards the same object at different angles, certain two sets of the photon counting detectors PCD1 through PCDN and the integrating detectors INTD1 through INTDN detectors detect simultaneously detect the corresponding transmitted X-ray from the two X-ray sources 101-1 and 101-2. Thus, because of the pair of the X-ray sources 101-1 and 101-2, the above describe exemplary embodiment acquires four sets of projection data from the two kinds of detectors.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique as already described with respect to FIG. 3. Furthermore, because of the pair of the X-ray sources 101-1 and 101-2, an additional set of projection data from the photon counting detectors PCD1 through PCDN potentially doubles temporal resolution. The integrating detectors INTD1 through INTDN also acquire a second pair of projection data, and the projection data from the integrating detectors INTD1 through INTDN is used to generally improve image quality. In acquiring the projection data, a sampling on the source trajectory is optionally made dense in order to enhance spatial resolution. On the other hand, software correction is optionally needed to reduce scatter in the acquired data as no anti-scatter gird is used in the channel direction on the hybrid detector. Furthermore, cross scatter optionally needs to be properly handled.

In the above embodiment, the photon counting detectors (PCD) and the integrating detectors (INTD) are fixedly placed along a first circular path around the object OBJ while the two X-ray sources 101-1 and 101-2 rotate along a second circular path around the same object OBJ. Furthermore, the above embodiment illustrates that the first circular path is larger and outside the second circular path around the object OBJ. Although it is not illustrated in a drawing, an additional alternative embodiment optionally reverses the relative relation of the first and second circular paths so that the second circular path for the X-ray sources 101-1 and 101-2 is larger and outside the first circular path of the sparsely placed photon counting detectors PCD1 through PCDN and the integrating detectors INTD1 through INTDN around the object OBJ to practice the current invention. Furthermore, the photon counting detectors PCD1 through PCDN are fixedly placed at either predetermined equidistant positions or predetermined non-equidistant positions on the circular component 200.

Figure 5:
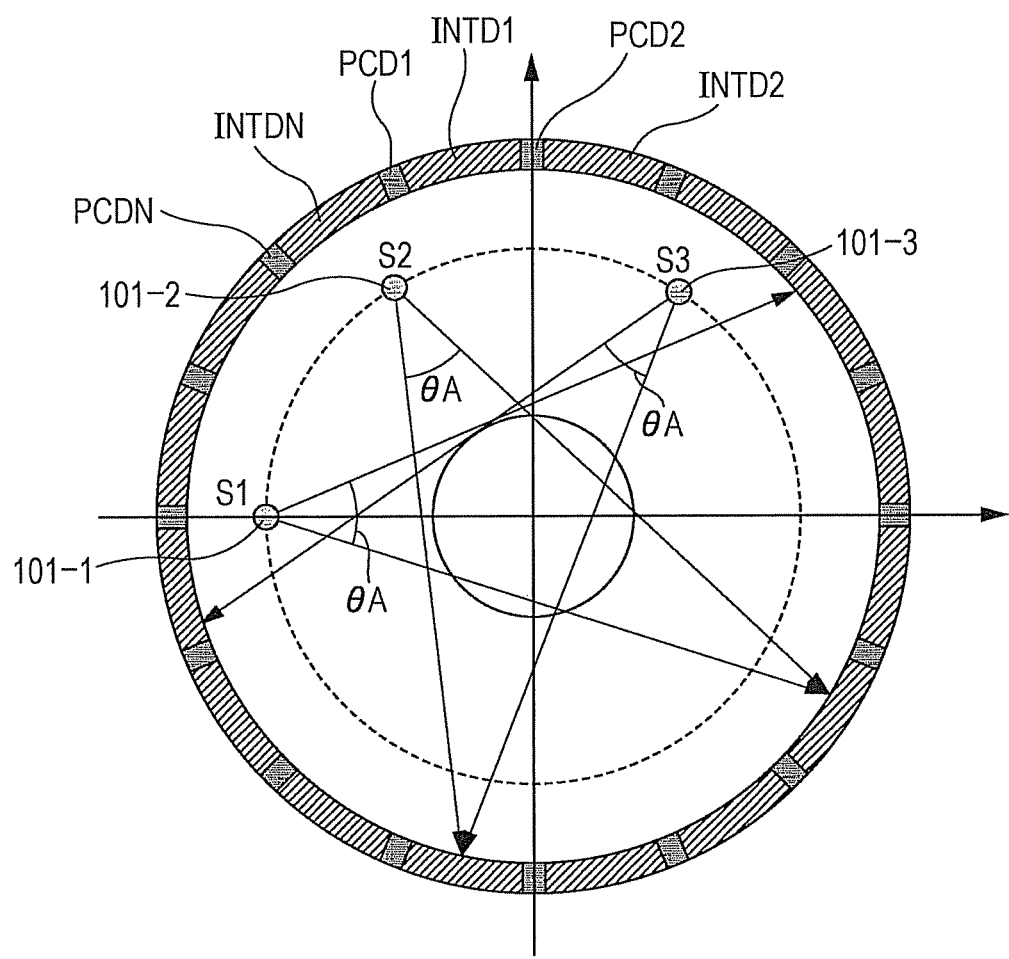
FIG. 5 is a diagram illustrating a third alternative embodiment including more than one X-ray source 101 and a hybrid detector in a predetermined fourth-generation geometry in the CT scanner system according to the current invention.

Now referring to FIG. 5, a diagram illustrates a third alternative embodiment including more than one X-ray source 101 and a hybrid detector in a predetermined fourth-generation geometry in the CT scanner system according to the current invention. One exemplary hybrid detector includes both the photon counting detectors (PCD) and integrating detectors (INTD) as described with respect to FIG. 3. The diagram merely illustrates a relative relationship among an object OBJ to be scanned, three of the X-ray sources 101, the photon counting detectors PCD1 through PCDN and the integrating detectors INTD1 through INTDN in one exemplary embodiment. For the sake of simplicity, the diagram excludes other components and units that are necessary in acquiring and processing data as well as reconstructing an image based upon the acquired data. The alternative embodiment optionally includes that the three X-ray sources 101-1, 101-2 and 101-3 are mounted at predetermined locations such as S1, S2 and S3 on the rotating portion 300 such as the annular frame 102 at a predetermined angle with each other. With respect to FIG. 5, certain other components and units may not be further described since they are substantially identical to those that are indicated by the same reference numerals and symbols in FIG. 2, 3 or 4.

The three X-ray sources 101-1, 101-2 and 101-3 are mounted at the locations S1, S2 and S3 on the rotating portion 300 such as the annular frame 102 in the gantry 100 and simultaneously rotate around the object OBJ about the same center. Although the angle between the positions S1 and S2 or the positions S2 and S3 on the rotating portion 300 is approximately 60 degrees in one exemplary alternative embodiment, the angle is not necessarily limited to a particular angle. As the rotating portion 300 rotates during the data acquisition, the X-ray sources 101-1, 101-2 and 101-3 each project X-ray with a predetermined source fan beam angle θA towards the object OBJ while the X-ray sources 101-1, 101-2 and 101-3 rotate around the object OBJ inside the sparsely placed photon counting detectors PCD1 through PCDN and the integrating detectors INTD1 through INTDN. Consequently, the photon counting detectors PCD1 through PCDN individually detect with a predetermined detector fan beam angle the X-ray that has been transmitted through the object OBJ and output a number of photons for each of predetermined energy components. At the same time, the integrating detectors INTD1 through INTDN also individually detect the X-ray that has been transmitted through the object OBJ and output a single value. Since the three X-ray sources 101-1, 101-2 and 101-3 simultaneously emit X-ray towards the same object at different angles, certain three sets of the photon counting detectors PCD1 through PCDN and the integrating detectors INTD1 through INTDN simultaneously detect the corresponding transmitted X-ray from the three X-ray sources 101-1, 101-2 and 101-3. Thus, because of the three X-ray sources 101-1, 101-2 and 101-3, the above describe exemplary embodiment acquires six sets of projection data from the two kinds of detectors.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique as already described with respect to FIG. 3. Furthermore, because of the three X-ray sources 101-1, 101-2 and 101-3, a triple set of projection data from the photon counting detectors PCD1 through PCDN potentially triples temporal resolution. The integrating detectors INTD1 through INTDN also acquire a triple set of projection data, and the projection data from the integrating detectors INTD1 through INTDN is used to generally improve image quality. In acquiring the projection data, a sampling on the source trajectory is optionally made dense in order to enhance spatial resolution. On the other hand, software correction is optionally needed to reduce scatter in the acquired data as no anti-scatter gird is used in the channel direction on the hybrid detector. Furthermore, cross scatter optionally needs to be properly handled.

In the above embodiment, the photon counting detectors (PCD) and the integrating detectors (INTD) are fixedly placed along a first circular path around the object OBJ while the three X-ray sources 101-1, 101-2 and 101-3 rotate along a second circular path around the same object OBJ. Furthermore, the above embodiment illustrates that the first circular path is larger and outside the second circular path around the object OBJ. Although it is not illustrated in a drawing, an additional alternative embodiment optionally reverses the relative relation of the first and second circular paths so that the second circular path for the X-ray sources 101-1, 101-2 and 101-3 is larger and outside the first circular path of the sparsely placed photon counting detectors PCD1 through PCDN and the integrating detectors INTD1 through INTDN around the object OBJ to practice the current invention. Furthermore, the photon counting detectors PCD1 through PCDN are fixedly placed at either predetermined equidistant positions or predetermined non-equidistant positions on the circular component 200.

With respect to FIGS. 3, 4 and 5, there are other alternative embodiments for placing the photon counting detectors (PCD) and the integrating detectors (INTD) in a predetermined fourth-generation geometry in the CT scanner system according to the current invention. At least one of the X-ray sources 101 is optionally a single energy source in certain alternative embodiments. By the same token, an additional alternative embodiment optionally includes the X-ray source 101, which is configured to perform a kV-switching function for emitting X-ray at a predetermined high-level energy and a predetermined low-level energy.

Figure 6:
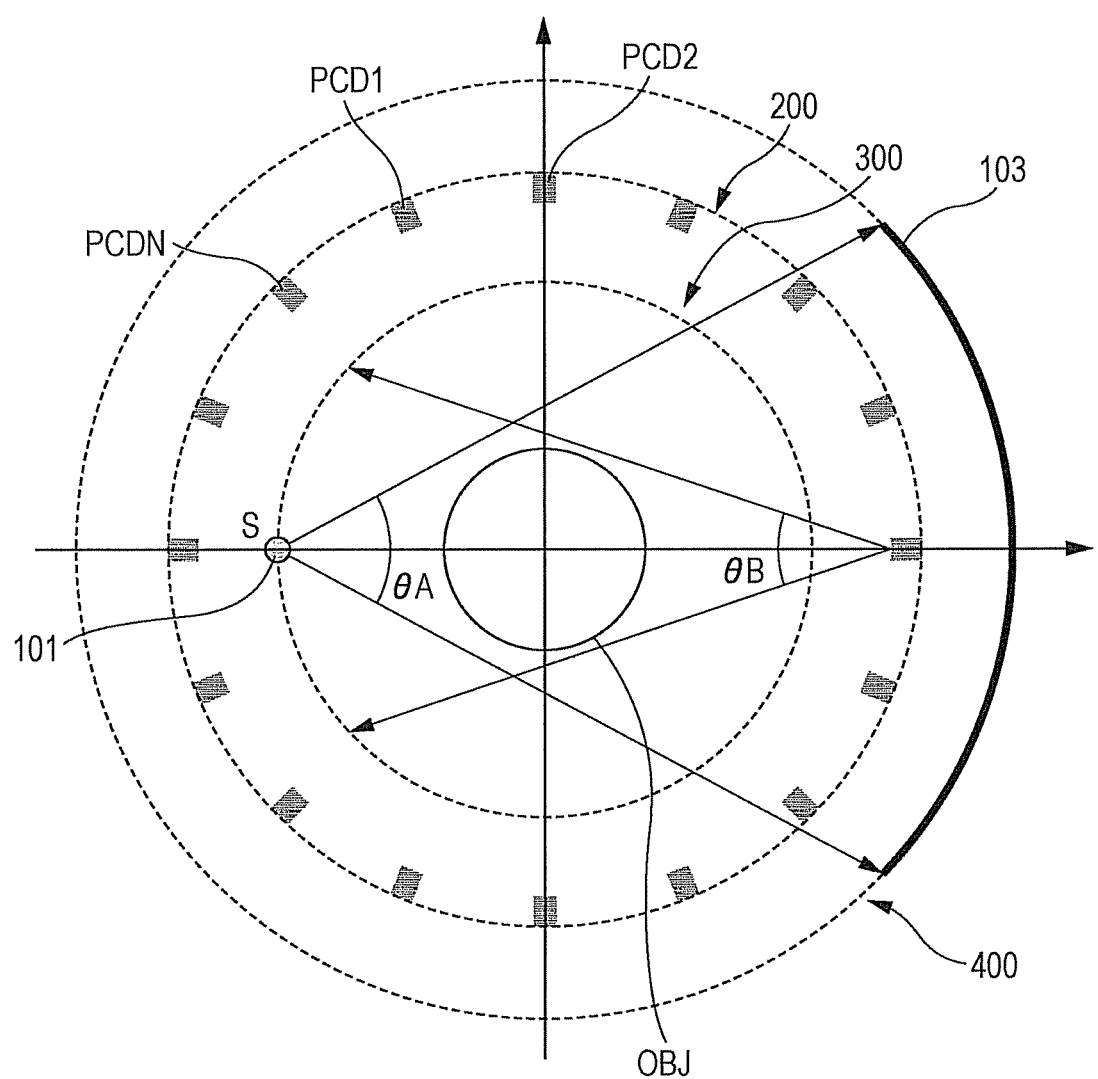
FIG. 6 is a diagram illustrating another embodiment for placing the photon counting detectors (PCD) in a predetermined fourth-generation geometry in combination with a detector unit in a predetermined third-generation geometry in the CT scanner system according to the current invention.

Now referring to FIG. 6, a diagram illustrates another embodiment for placing the photon counting detectors (PCD) in a predetermined fourth-generation geometry in combination with a detector unit in a predetermined third-generation geometry in the CT scanner system according to the current invention. The diagram merely illustrates a relative relationship among an object OBJ to be scanned, an X-ray source 101, a X-ray detector 103 and the photon counting detectors PCD1 through PCDN in one exemplary embodiment. For the sake of simplicity, the diagram excludes other components and units that are necessary in acquiring and processing data as well as reconstructing an image based upon the acquired data. In general, the photon counting detectors PCD1 through PCDN are each a commercially available device and output a photon count for each of predetermined energy components. Although approximately one hundred to three hundred photon counting detectors are utilized in certain embodiments, the above numerical range of the photon counting detectors is merely exemplary, and the claimed invention is not necessarily limited to any particular number of the photon counting detectors. In addition to the sparse photon counting detectors PCD1 through PCDN in the fourth-generation geometry, the embodiment of FIG. 6 now further includes a detector unit such as the detector 103 in a predetermined third-generation geometry in the CT scanner system according to the current invention. The detector elements in the detector unit 103 are generally more densely placed along the detector unit surface than the photon counting detectors (PCD) in the exemplary embodiment.

Still referring to FIG. 6, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition.

Both the X-ray source 101 and the detector unit 103 rotate around the object OBJ while the photon counting detectors PCD1 through PCDN are stationary with respect to the object OBJ. In one exemplary embodiment, the X-ray source 101 is mounted on a first rotating portion 300 such as the annular frame 102 in the gantry 100 so that the X-ray source 101 projects X-ray with a predetermined source fan beam angle θA towards the object OBJ while the X-ray source 101 rotates around the object OBJ inside the sparsely placed photon counting detectors PCD1 through PCDN. Furthermore, an additional detector unit 103 is mounted on a second rotating portion 400 in the third-generation geometry in the above exemplary embodiment of the CT scanner system according to the current invention. The rotating portion 400 mounts the detector unit 103 at a diametrically opposed position from the X-ray source 101 across the object OBJ and rotates outside the stationary circular component 200, on which the photon counting detectors PCD1 through PCDN are fixedly placed in a predetermined sparse manner.

In one implementation, the rotating portions 300 and 400 are integrally constructed as a single component such as the annular frame 102 to maintain the 180-degree angle between the X-ray source 101 and the detector unit 103 as they rotate about the object OBJ with a different radius. In an optional implementation, the rotating portions 300 and 400 are separate components but synchronously rotate to maintain the X-ray source 101 and the detector unit 103 in the fixedly opposed positions at 180 degrees across the object OBJ. Furthermore, the X-ray source 101 optionally travels a helical path as the object is moved in a predetermined direction that is perpendicular to the rotational plane of the rotating portion 300.

As the X-ray source 101 and the detector unit 103 rotate around the object OBJ, the photon counting detectors PCDs and the detector unit 103 respectively detect the transmitted X-ray during the data acquisition. The photon counting detectors PCD1 through PCDN intermittently detect with a predetermined detector fan beam angle θB the X-ray that has been transmitted through the object OBJ and individually output a number of photons for each of predetermined energy components. On the other hand, the detector elements in the detector unit 103 continuously detect the X-ray that has been transmitted through the object OBJ and outputs the detected signals as the detector unit 103 rotates. Although the additional characteristics of the detector elements in the detector unit 103 will be later described in details, one implementation of the detector unit 103 has densely placed integrating detectors in a predetermined channel and segment directions on the detector unit surface.

In the above exemplary embodiment, the X-ray source 101, the photon counting detectors (PCD) and the detector unit 103 collectively form three predetermined circular paths that differ in radius. The photon counting detectors (PCD) are sparsely placed along a first circular path around the object OBJ while at least one X-ray source 101 rotates along a second circular path around the object OBJ. Further, the detector unit 103 travels along a third circular path. The above exemplary embodiment illustrates that the third circular path is the largest and outside the first and second circular paths around the object OBJ. Although it is not illustrated in a drawing, an alternative embodiment optionally changes the relative relation of the first and second circular paths so that the second circular path for the X-ray source 101 is larger and outside the first circular path of the sparsely placed photon counting detectors PCD1 through PCDN around the object OBJ to practice the current invention. Furthermore, in another alternative embodiment, the X-ray source 101 also optionally travels on the same third circular path as the detector unit 103. Furthermore, the above alternative embodiments optionally provide a protective rear cover for each of the photon counting detectors (PCD) that are irradiated from behind in a short distance as the X-ray source 101 travels outside the first circular path of the sparsely placed photon counting detectors (PCD).

There are other alternative embodiments for placing the photon counting detectors (PCD) in a predetermined fourth-generation geometry in combination with the detector unit in a predetermined third-generation geometry in the CT scanner system according to the current invention. The X-ray source 101 is optionally a single energy source in certain embodiments. By the same token, an additional alternative embodiment optionally includes the X-ray source 101, which is configured to perform a kV-switching function for emitting X-ray at a predetermined high-level energy and a predetermined low-level energy.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique as already described with respect to FIG. 3. In addition, the detector unit 103 also acquires another set of projection data, and the projection data from the detector unit 103 is used to generally improve image quality. In case that the detector unit 103 consists of integrating detectors (INTD) with anti-scatter grids, the projection data from the detector unit 103 is used to correct scatter on the projection data from the photon counting detectors (PCD). In the above alternative embodiments, the integrating detectors (INTD) optionally need to be calibrated in view of X-ray transmission through the predetermined circular component 200 and some of the photon counting detectors (PCD). In acquiring the projection data, a sampling on the source trajectory is optionally made dense in order to enhance spatial resolution.

Figure 7:
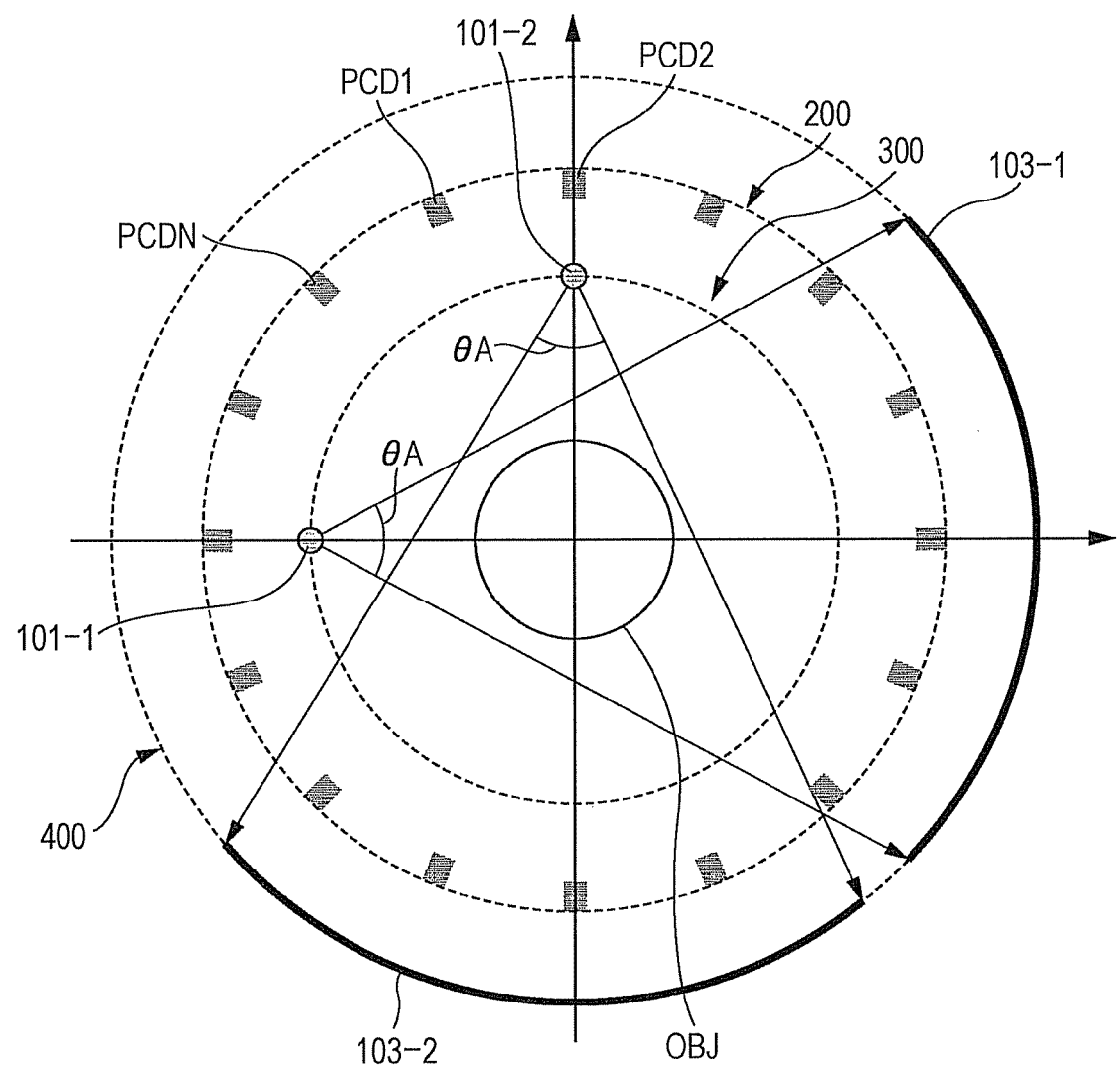
FIG. 7 is a diagram illustrating another embodiment for placing the photon counting detectors (PCD) in a predetermined fourth-generation geometry in combination with two X-ray sources and two detector units in a predetermined third-generation geometry in the CT scanner system according to the current invention.

Now referring to FIG. 7, a diagram illustrates another embodiment for placing the photon counting detectors (PCD) in a predetermined fourth-generation geometry in combination with two X-ray sources and two detector units in a predetermined third-generation geometry in the CT scanner system according to the current invention. The diagram merely illustrates a relative relationship among an object OBJ to be scanned, two X-ray sources 101-1 and 101-2, two X-ray detector units 103-1 and 103-2 and the photon counting detectors PCD1 through PCDN in one exemplary embodiment. For the sake of simplicity, the diagram excludes other components and units that are necessary in acquiring and processing data as well as reconstructing an image based upon the acquired data. As already described, although approximately one hundred to three hundred commercially available photon counting detectors PCD1 through PCDN are generally utilized in certain embodiments, the above numerical range of the photon counting detectors is merely exemplary, and the claimed invention is not necessarily limited to any particular number of the photon counting detectors. In addition to the sparse photon counting detectors PCD1 through PCDN in the fourth-generation geometry, the exemplary embodiment of FIG. 7 now further includes at least two detector units in a predetermined third-generation geometry in the CT scanner system according to the current invention.

Still referring to FIG. 7, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition.

The two pairs of the X-ray sources 101-1, 101-2 and the detector units 103-1, 103-2 rotate around the object OBJ while the photon counting detectors PCD1 through PCDN are stationary with respect to the object OBJ. For each pair, a rotating portion 400 respectively mounts the detector units 103-1 and 103-2 at a diametrically opposed position from the X-ray sources 101-1 and 101-2 across the object OBJ and rotates outside the stationary circular component 200, on which the photon counting detectors PCD1 through PCDN are fixedly placed in a predetermined sparse manner. Furthermore, a first pair of the X-ray source 101-1 and the detector unit 103-1 is mounted in a substantially perpendicular manner with respect to a second pair of the X-ray source 101-2 and the detector unit 103-2 on a first rotating portion 300 such as the annular frame 102 in the gantry 100 in the above exemplary embodiment. Each of the X-ray sources 101-1 and 101-2 projects X-ray with a predetermined source fan beam angle θA towards the object OBJ while the X-ray sources 101-1 and 101-2 rotate around the object OBJ inside the sparsely placed photon counting detectors PCD1 through PCDN.

In one implementation, the rotating portions 300 and 400 are integrally constructed as a single component such as the annular frame 102 to maintain the 180-degree angle between the X-ray sources 101-1, 101-2 and the detector units 103-1, 103-2 as they rotate about the object OBJ with a different radius. In an optional implementation, the rotating portions 300 and 400 are separate components but synchronously rotate to maintain the X-ray sources 101-1, 101-2 and the detector units 103-1, 103-2 in the fixedly opposed positions at 180 degrees across the object OBJ. Furthermore, the X-ray sources 101-1 and 101-2 optionally travel a helical path as the object is moved in a predetermined direction that is perpendicular to the rotational plane of the rotating portion 300.

As the X-ray sources 101-1, 101-2 and the detector units 103-1, 103-2 rotate around the object OBJ, the photon counting detectors (PCD) and the detector units 103-1, 103-2 respectively detect the transmitted X-ray during the data acquisition. The photon counting detectors PCD1 through PCDN intermittently detect with a predetermined detector fan beam angle θB the X-ray that has been transmitted through the object OBJ and individually output a number of photons for each of predetermined energy components. On the other hand, the detector elements in the detector units 103-1 and 103-2 continuously detect the X-ray that has been transmitted through the object OBJ and output the detected signals as the detector units 103-1 and 103-2 rotate. Although the additional characteristics of the detector elements in the detector units 103-1 and 103-2 will be later described in details, one implementation of the detector units 103-1 and 103-2 has densely placed integrating detectors in a predetermined channel and segment directions on the detector unit surface.

In the above exemplary embodiment, the X-ray sources 101-1, 101-2, the photon counting detectors (PCD) and the detector units 103-1, 103-2 collectively form three predetermined circular paths that differ in radius. The photon counting detectors (PCD) are sparsely placed along a first circular path around the object OBJ while the X-ray sources 101-1 and 101-2 rotate along a second circular path around the object OBJ. Further, the detector units 103-1 and 103-2 both travel along a third circular path. The above exemplary embodiment illustrates that the third circular path is the largest and outside the first and second circular paths around the object OBJ. Although it is not illustrated in a drawing, an alternative embodiment optionally changes the relative relation of the first and second circular paths so that the second circular path for the X-ray sources 101-1 and 101-2 is larger and outside the first circular path of the sparsely placed photon counting detectors PCD1 through PCDN around the object OBJ to practice the current invention. Furthermore, in another alternative embodiment, the X-ray sources 101-1 and 101-2 also optionally travel on the same third circular path as the detector units 103-1 and 103-2. Furthermore, the above alternative embodiments optionally provide a protective rear cover for each of the photon counting detectors (PCD) that are irradiated from behind in a short distance as the X-ray sources 101-1 and 101-2 travel outside the first circular path of the sparsely placed photon counting detectors (PCD).

There are other alternative embodiments for placing the photon counting detectors (PCD) in a predetermined fourth-generation geometry in combination with two sources and two detector units in a predetermined third-generation geometry in the CT scanner system according to the current invention. At least one of the X-ray sources 101-1 and 101-2 is optionally a single energy source in certain embodiments. By the same token, an additional alternative embodiment optionally includes the X-ray sources 101-1 and or 101-2, which are configured to perform a kV-switching function for emitting X-ray at a predetermined high-level energy and a predetermined low-level energy.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique as already described with respect to FIG. 3. In addition, the detector units 103-1 and 103-2 respectively acquire another set of projection data, and the projection data from the detector units 103-1 and 103-2 is used to generally improve image quality. In case that the detector units 103-1 and 103-2 consist of integrating detectors (INTD) with anti-scatter grids, the projection data from the detector units 103-1 and 103-2 is used to correct scatter on the projection data from the photon counting detectors (PCD). In the above alternative embodiments, the integrating detectors (INTD) optionally need to be calibrated in view of X-ray transmission through the predetermined circular component 200 and some of the photon counting detectors (PCD). In acquiring the projection data, a sampling on the source trajectory is optionally made dense in order to enhance spatial resolution.

Figure 8:
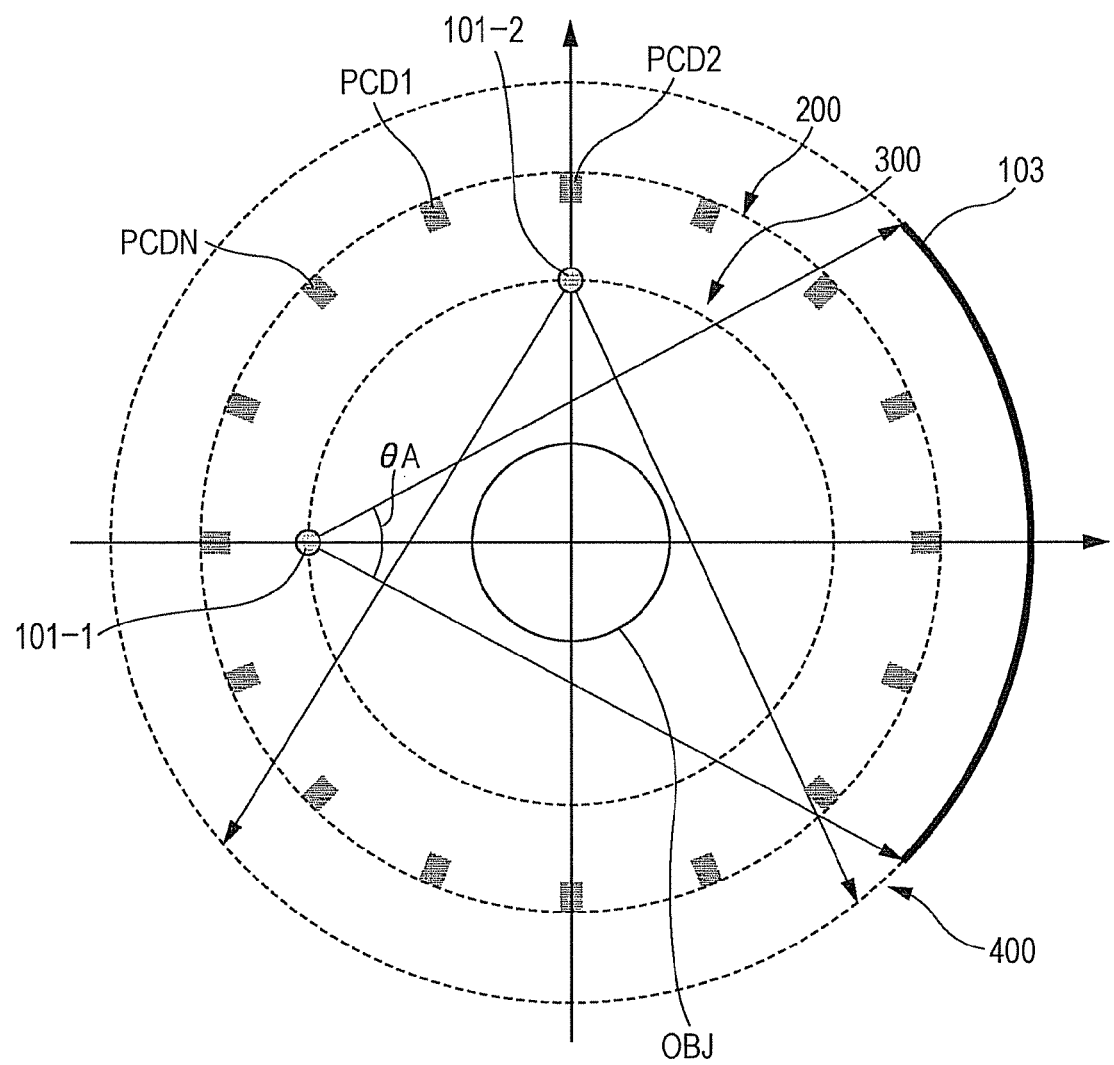
FIG. 8 is a drawing illustrating an alternative embodiment for placing the photon counting detectors (PCD) in a predetermined fourth-generation geometry in combination with two X-ray sources with only one corresponding detector unit a predetermined third-generation geometry in the CT scanner system according to the current invention.

Now referring to FIG. 8, a drawing illustrates an alternative embodiment for placing the photon counting detectors (PCD) in a predetermined fourth-generation geometry in combination with two X-ray sources with only one corresponding detector unit in a predetermined third-generation geometry in the CT scanner system according to the current invention. The diagram merely illustrates a relative relationship among an object OBJ to be scanned, two X-ray sources 101-1 and 101-2, one X-ray detector units 103 and the photon counting detectors PCD1 through PCDN in one exemplary embodiment. For the sake of simplicity, the diagram excludes other components and units that are necessary in acquiring and processing data as well as reconstructing an image based upon the acquired data. As already described, although approximately one hundred to three hundred commercially available photon counting detectors PCD1 through PCDN are generally utilized in certain embodiments, the above numerical range of the photon counting detectors is merely exemplary, and the claimed invention is not necessarily limited to any particular number of the photon counting detectors. In addition to the sparse photon counting detectors PCD1 through PCDN in the fourth-generation geometry, the exemplary embodiment of FIG. 8 now further includes a single detector unit 103 in a predetermined third-generation geometry for detecting transmitted X ray substantially from either one of the two X-ray sources 101-1 and 101-2 in the CT scanner system according to the current invention.

Still referring to FIG. 8, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition.

The two pairs of the X-ray sources 101-1, 101-2 and the single detector unit 103 rotate around the object OBJ while the photon counting detectors PCD1 through PCDN are stationary with respect to the object OBJ. The rotating portion 400 mounts the detector unit 103 at a diametrically opposed position from the X-ray sources 101-1 across the object OBJ and rotates outside the stationary circular component 200, on which the photon counting detectors PCD1 through PCDN are fixedly placed in a predetermined sparse manner. Furthermore, the pair of the X-ray source 101-1 and the detector unit 103 is mounted in a substantially perpendicular manner with respect to the central projection direction of the X-ray source 101-2 on a first rotating portion 300 such as the annular frame 102 in the gantry 100 in the above exemplary embodiment. Each of the X-ray sources 101-1 and 101-2 projects X-ray with a predetermined source fan beam angle θ A towards the object OBJ while the X-ray sources 101-1 and 101-2 rotate around the object OBJ inside the sparsely placed photon counting detectors PCD1 through PCDN.

In one implementation, the rotating portions 300 and 400 are integrally constructed as a single component such as the annular frame 102 to maintain the 180-degree angle between the X-ray sources 101-1 and the detector unit 103 as they rotate about the object OBJ with a different radius. In an optional implementation, the rotating portions 300 and 400 are separate components but synchronously rotate to maintain the X-ray source 101-1 and the detector unit 103 in the fixedly opposed positions at 180 degrees across the object OBJ. Furthermore, the X-ray sources 101-1 and 101-2 optionally travel a helical path as the object is moved in a predetermined direction that is perpendicular to the rotational plane of the rotating portion 300.

As the X-ray sources 101-1, 101-2 and the detector unit 103 rotate around the object OBJ, the photon counting detectors (PCD) and the detector unit 103 respectively detect the transmitted X-ray during the data acquisition. The photon counting detectors PCD1 through PCDN intermittently detect with a predetermined detector fan beam angle θ B the X-ray that has been transmitted through the object OBJ and individually output a number of photons for each of predetermined energy components. On the other hand, the detector elements in the detector unit 103 continuously detect the X-ray that has been transmitted through the object OBJ and output the detected signals as the detector unit 103 rotates. Although the additional characteristics of the detector elements in the detector unit 103 will be later described in details, one implementation of the detector unit 103 has densely placed integrating detectors in a predetermined channel and segment directions on the detector unit surface.

In the above exemplary embodiment, the X-ray sources 101-1, 101-2, the photon counting detectors (PCD) and the detector unit 103 collectively form three predetermined circular paths that differ in radius. The photon counting detectors (PCD) are sparsely placed along a first circular path around the object OBJ while the X-ray sources 101-1 and 101-2 rotate along a second circular path around the object OBJ. Further, the detector unit 103 travels along a third circular path. The above exemplary embodiment illustrates that the third circular path is the largest and outside the first and second circular paths around the object OBJ. Although it is not illustrated in a drawing, an alternative embodiment optionally changes the relative relation of the first and second circular paths so that the second circular path for the X-ray sources 101-1 and 101-2 is larger and outside the first circular path of the sparsely placed photon counting detectors PCD1 through PCDN around the object OBJ to practice the current invention. Furthermore, in another alternative embodiment, the X-ray sources 101-1 and 101-2 also optionally travel on the same third circular path as the detector unit 103. Furthermore, the above alternative embodiments optionally provide a protective rear cover for each of the photon counting detectors (PCD) that are irradiated from behind in a short distance as the X-ray sources 101-1 and 101-2 travel outside the first circular path of the sparsely placed photon counting detectors (PCD).

There are other alternative embodiments for placing the photon counting detectors (PCD) in a predetermined fourth-generation geometry in combination with two sources and one detector unit in a predetermined third-generation geometry in the CT scanner system according to the current invention. At least one of the X-ray sources 101-1 and 101-2 is optionally a single energy source in certain embodiments. By the same token, an additional alternative embodiment optionally includes the X-ray sources 101-1 and or 101-2, which are configured to perform a kV-switching function for emitting X-ray at a predetermined high-level energy and a predetermined low-level energy.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique as already described with respect to FIG. 3. In addition, the detector unit 103 acquires another set of projection data, and the projection data from the detector unit 103 is used to generally improve image quality. In case that the detector unit 103 consists of integrating detectors (INTD) with anti-scatter grids, the projection data from the detector unit 103 is used to correct scatter on the projection data from the photon counting detectors (PCD). In the above alternative embodiments, the integrating detectors (INTD) optionally need to be calibrated in view of X-ray transmission through the predetermined circular component 200 and some of the photon counting detectors (PCD). In acquiring the projection data, a sampling on the source trajectory is optionally made dense in order to enhance spatial resolution.

Figure 9:
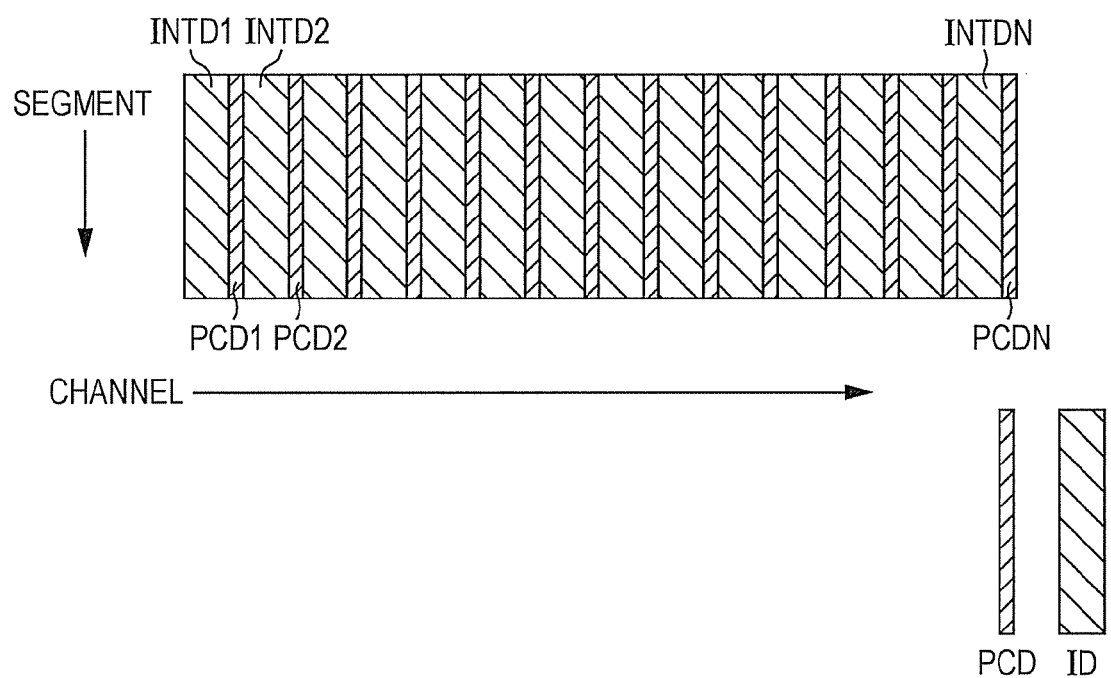
FIG. 9 is a diagram illustrating one embodiment of a basic hybrid detector in the CT scanner system according to the current invention.

Now referring to FIG. 9, a diagram illustrates one embodiment of a basic hybrid detector in the CT scanner system according to the current invention. In one embodiment of the hybrid detector, the detector array 103A includes a plurality of photon counting detectors (PCD) and integrating detectors (INTD) in a predetermined alternating pattern. The detector elements are placed in the segment direction and the channel direction as respectively indicated by the arrows in the detector array 103A. Along the channel direction, the photon counting detector (PCD) units or the photon counting detectors (PCD) are sparsely and equidistantly placed at the fixed positions in one embodiment according to the current invention. In the illustrated embodiment, the integrating detector (INTD) units or the integrating detectors (INTD) are placed between the two adjacent ones of the photon counting detector (PCD) units except one on the first integrating detector unit INTD1. Each of the photon counting detector (PCD) units consists of N×1 PCD detector elements while each of the integrating detector (INTD) units consists of N×M such as 64×24 integrating detector elements. Because of the above difference in the channel size, the photon counting detectors (PCD) are sparsely located in the channel direction with respect to the integrating detectors (INTD).

Still referring to FIG. 9, the hybrid detector is used in the detector unit in the third-generation geometry and or the fourth-generation geometry. The detector array 103A forms an arc whose middle portion is centered at a predetermined x-ray source in a third generation CT geometry. The detector array 103A is mounted on the surface of the detector unit 103 in one embodiment. The detector array 103A also optionally forms a cylinder whose center is configured at the iso-center in the fourth generation CT geometry. In another embodiment, the PCDs and INTDs are optionally placed on different surfaces such as tunnel or grid for substantially reducing scatter during sampling. Other embodiments of the hybrid detector are not limited to the illustrated pattern or the above specified row/column configurations. One alternative embodiment includes only sparsely positioned photon counting detectors (PCD) at the predetermined equidistant positions without the integrating detectors (INTD).

Now referring to FIGS. 10A and 10B, the diagrams respectively depict sparse views and sparse detectors. FIG. 10A is a diagram illustrating the relationship among the source positions P1 through PN, the field of view (FOV) and an arbitrary image point A in the FOV in sparse view sampling. As indicated by a limited number of the source positions P1 through PN, sparse view sampling yields that projections passing through the point A in the FOV are sparse in directions. By the same token, any point in the FOV has a similar sparse sampling level.

FIG. 10B is a diagram illustrating a sparsity level of the detectors in accordance with the radius in sparse detector sampling. Each circle represents a photon counting detector while each line tangent to the circle represents sample data bearing spectral information. The radius is defined to be a distance between an arbitrary image point B and the isocenter IC. The diagram indicates that as the radius increases, a number of tangent lines to the circles increases within the given radius. The increased number of the tangent lines signifies a denser level of sampling. On the other hand, the diagram also indicates that as the radius decreases, a number of tangent lines to the circles decreases within the given radius. The decreased number of the tangent lines signifies a sparser level of sampling. In general, a central region has a sparser sampling level while a peripheral region has a denser level of sampling. In addition, the angular range of projections is less than 180°.

Based upon the above relation as described with respect to FIG. 10B, the photon counting detector (PCD) units or the photon counting detectors (PCD) are not equidistantly placed at the fixed positions in one embodiment according to the current invention. That is, a larger number of the photon counting detectors (PCD) are used to cover the central region while a smaller number of the PCDs are used to cover the peripheral region in one embodiment. The embodiment in the above described configuration substantially reduces the pile-up effect while it also substantially reduces the high costs associated with the PCDs.

Now referring to FIGS. 11A, 11B and 11C, the diagrams respectively depict various non-equidistant configuration patterns of the photon counting detectors (PCD) and the integrating counters (ITGD) in certain embodiments of the hybrid detector in the CT scanner system according to the current invention. In FIGS. 11A and 11B, it is assumed that pile-up does not occur in the central region but does occur in the peripheral regions. For these reasons, central photon counting detectors PCD-C are exclusively and densely placed near or within the central region in the channel direction. On the other hand, peripheral photon counting detectors PCD1 through PCDN are sparsely placed outside the central region in the channel direction. In combination with the peripheral photon counting detectors PCD1 through PCDN, integrating detectors INTD1 through INTDN are respectively placed between two adjacent ones of the photon counting detectors PCD1 through PCDN. For example, the integrating detector INTD2 is placed between the two adjacent photon counting detectors PCD1 and PCD2.

In FIG. 11C, pile-up is allowed anywhere, and proper correction is performed according to neighboring integrating detectors INTS. Although central photon counting detectors PCD-C are more densely placed near or within the central region than in the peripheral regions in the channel direction, the central photon counting detectors PCD-C are not exclusive in the central region. At the same time, peripheral photon counting detectors PCD1 through PCDN are sparsely placed outside the central region in the channel direction. In combination with the peripheral photon counting detectors PCD1 through PCDN, integrating detectors INTD1 through INTDN are respectively placed between two adjacent ones of the photon counting detectors PCD1 through PCDN.

Figure 12:
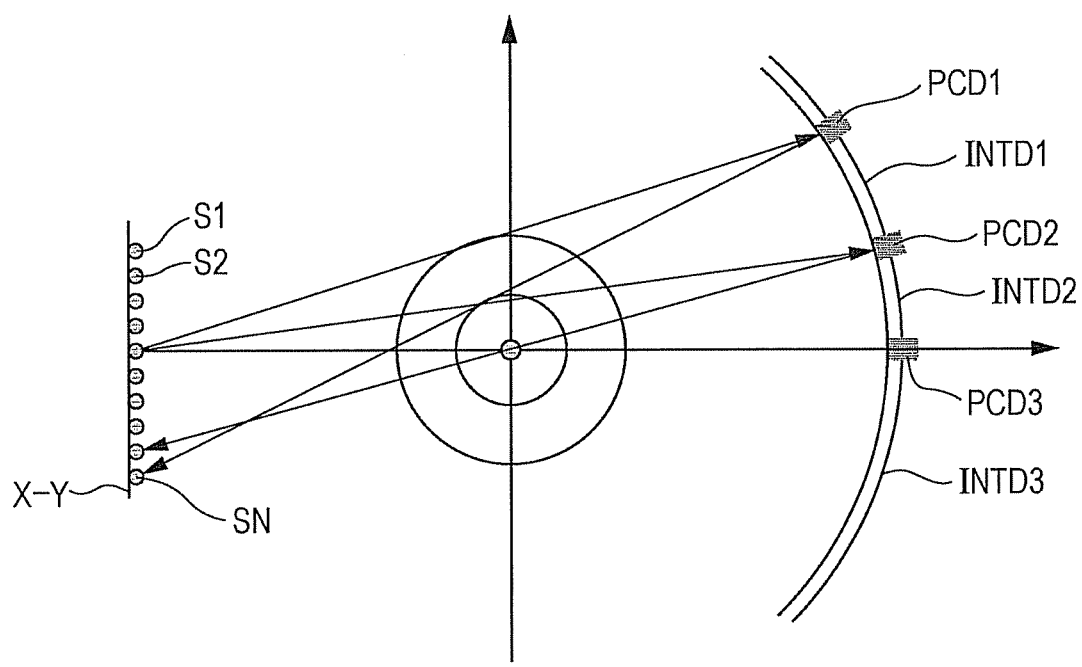
FIG. 12 is a diagram illustrating sparsely placed photon counting detectors and integrating detectors in combination with fly focal spot in the CT scanner system according to the current invention.

Now referring to FIG. 12, a diagram illustrates sparsely placed photon counting detectors and integrating detectors in combination with fly focal spot in the CT scanner system according to the current invention. On the right hand side, the diagram partially illustrates sparsely placed photon counting detectors PCD1 through PCD3 and the integrating detectors INTD1 and INTD2 that are respectively placed between the two adjacent photon counting detectors PCD1 through PCD3 on the same surface with no tunnel without anti-scatter grid on the integrating detectors. In the center of the diagram, the two concentric circles and a concentric center respectively signify the photon counting detectors PCD1 through PCD3. On the left hand side, the diagram partially illustrates the projections from the source to the photon counting detectors PCD1 through PCD3. The source position is optionally moved by fly focal spots on a predetermined X-Y plane in one embodiment. The source position is optionally moved by fly focal spots in the Z-direction in addition to a predetermined X-Y plane in another embodiment. The tangential points on the central circles indicate the measured data.

Still referring to FIG. 12, data sufficiency improves with fly focal spot. Sparse photon counting detectors (PCD) with a fixed focal spot may not provide sufficient data for dual energy (DE) reconstruction. On the other hand, fly focal spot combined with sparse photon counting detectors (PCD) optionally provide sufficient data. Furthermore, data from integrating detectors (INTD) are redundant with fly focal spot for optionally improving image quality in terms of noise and resolution. Software correction is optionally needed to reduce scatter in the acquired data. In an iterative reconstruction, software scatter correction proves to be accurate.

Now referring to FIG. 13, a flow chart illustrates steps or acts involved in a process or method of acquiring data for spectral CT using sparse photon counting detectors according to the current invention. The flow chart merely depicts the acts or steps involving an object to be scanned, an X-ray source and the photon counting detectors in one exemplary embodiment. For the sake of simplicity, the flow chart excludes the acts or steps involving other components and units that are necessary in acquiring and processing data as well as reconstructing an image based upon the acquired data. In general, the photon counting detectors are each a commercially available device and output a photon count for each of predetermined energy components.

In a step S100, approximately one hundred to three hundred photon counting detectors are sparsely placed on a stationary component around an object to be scanned in a predetermined fourth-generation geometry such as a first circular path around the object. The circular component remains stationary with respect to the object and fails to rotate during the data acquisition. In one embodiment, the photon counting detectors are fixedly placed at predetermined equidistant positions while in another embodiment the photon counting detectors are fixedly placed at predetermined non-equidistant positions. The above numerical range of the photon counting detectors is merely exemplary, and the claimed invention is not necessarily limited to any particular number of the photon counting detectors.

In a step S200, at least a single X-ray source is mounted on a rotating portion such as the annular frame in the gantry. The annular frame is a second circular path also around the object. In one process, the first circular path along which the photon counting detectors are sparsely placed is larger and outside the second circular path on which the X-ray source is mounted. In another process, the second circular path for the X-ray source is optionally larger and outside the first circular path of the sparsely placed photon counting detectors around the object to practice the current invention. In yet another process, a plurality of the X-ray sources is mounted on the rotating portion at a predetermined angle with each other.

In a step S300, the X-ray source rotates around the object. In one process, the X-ray source rotates around the object inside the sparsely placed photon counting detectors in the step S300. In another process, the X-ray source rotates around the object outside the sparsely placed photon counting detectors in the step S300, in which an additional step is optionally needed to protect the photon counting detectors that receive the X-ray from the behind in a short distance.

In a step S400, the X-ray source emits X-ray with a predetermined source fan beam angle towards the object while it simultaneously rotates in the step S300 in one process. At least one of the X-ray sources is optionally a single energy source in a certain process. By the same token, an alternative process optionally includes the X-ray source, which is configured to perform a kV-switching function for emitting X-ray at a predetermined high-level energy and a predetermined low-level energy in the step S400.

In a step S500, the photon counting detectors individually detect with a predetermined detector fan beam angle the X-ray that has been transmitted through the object in the step S400. The photon counting detectors output a photon count for each of predetermined energy components. Thus, the step S500 acquires data.

The above described steps or acts of the process are merely illustrative, and the process of acquiring data operates in different manners for spectral CT using sparse photon counting detectors according to the current invention. Although the steps S100 through S500 are described in a single sequence of events or acts in one process, some of the steps in the process are repetitively performed while others are only initially performed. Furthermore, some steps of the process are simultaneously performed during the repetitive performance.

Now referring to FIG. 14, a flow chart illustrates steps or acts involved in a process or method of acquiring data for spectral CT using a combination of sparse photon counting detectors and integrating detectors according to the current invention. The flow chart merely depicts the acts or steps involving an object to be scanned, an X-ray source, the integrating detectors and the photon counting detectors in one exemplary embodiment. For the sake of simplicity, the flow chart excludes the acts or steps involving other components and units that are necessary in acquiring and processing data as well as reconstructing an image based upon the acquired data. In general, the photon counting detectors are each a commercially available device and output a photon count for each of predetermined energy components.

In a step S1000, approximately one hundred to three hundred photon counting detectors are sparsely placed on a stationary component around an object to be scanned in a predetermined fourth-generation geometry such as a first circular path around the object. The circular component remains stationary with respect to the object and fails to rotate during the data acquisition. In one embodiment, the photon counting detectors are fixedly placed at predetermined equidistant positions while in another embodiment the photon counting detectors are fixedly placed at predetermined non-equidistant positions. The above numerical range of the photon counting detectors is merely exemplary, and the claimed invention is not necessarily limited to any particular number of the photon counting detectors.

In a step S1100, an X-ray source and a detector unit are mounted on a rotating portion. At least a single X-ray source is mounted on a first rotating portion such as the annular frame in the gantry. The annular frame is a second circular path also around the object. In one process, the first circular path along which the photon counting detectors are sparsely placed is larger and outside the second circular path on which the X-ray source is mounted. In another process, the second circular path for the X-ray source is optionally larger and outside the first circular path of the sparsely placed photon counting detectors around the object to practice the current invention. In yet another process, a plurality of the X-ray sources is mounted on the rotating portion at a predetermined angle with each other.

Also in the step S1100, the detector unit is mounted on a second rotating portion in the third-generation geometry outside the sparsely placed photon counting detectors in the step S1000. In one process, the detector unit consists of a plurality of integrating detector elements. In another process, the detector unit consists of a combination of integrating detector elements and photon counting detector elements in a predetermined configuration. In one process, the first rotating portion and the second rotating portions are farmed in an integral manner. In another process, the first rotating portion and the second rotating portions are separately formed and independently rotatable.

In a step S1200, the X-ray source and the detector unit rotate around the object. In one process, the X-ray source rotates around the object inside the sparsely placed photon counting detectors in the step S1200. In another process, the X-ray source rotates around the object outside the sparsely placed photon counting detectors in the step S1200, in which an additional step is optionally needed to protect the photon counting detectors that receive the X-ray from the behind in a short distance. In the step S1200, the detector unit also rotates around the object. In one process, the detector unit rotates around the object outside the sparsely placed photon counting detectors in the step S1000.

In a step S1300, the X-ray source emits X-ray with a predetermined source fan beam angle towards the object while it simultaneously rotates in the step S1200 in one process. At least one of the X-ray sources is optionally a single energy source in a certain process. By the same token, an alternative process optionally includes the X-ray source, which is configured to perform a kV-switching function for emitting X-ray at a predetermined high-level energy and a predetermined low-level energy in the step S1300.

In a step S1400, the photon counting detectors individually detect with a predetermined detector fan beam angle the X-ray that has been transmitted through the object in the step S1300. The photon counting detectors output a photon count for each of predetermined energy components. In the step S1400, the detector unit also detects the X-ray that has been transmitted through the object in the step S1300. Thus, the step S1400 acquires data.

The above described steps or acts of the process are merely illustrative, and the process of acquiring data operates in different manners for spectral CT using sparse photon counting detectors according to the current invention. Although the steps S1000 through S1400 are described in a single sequence of events or acts in one process, some of steps in the process are repetitively performed while others are only initially performed. Furthermore, some steps of the process are simultaneously performed during the repetitive performance.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A spectral CT apparatus, comprising:
   a first rotating portion for rotating around an object;
   at least one source for emitting X-ray mounted at a first predetermined position on said first rotating portion for travelling along a predetermined path with respect to the object;
   a predetermined number of photon counting detectors sparsely placed at fixed positions along a predetermined circle around the object to be scanned;
   a second rotating portion for rotating around the object; and
   a detector unit having integrating detectors located at a second predetermined position on said second rotating portion, wherein said second rotating portion has a larger diameter than the predetermined circle along which said photon counting detectors are sparsely placed at the fixed positions.

2. The spectral CT apparatus according to claim 1 wherein the predetermined path of said at least one source is located inside the predetermined circle on which the said photon counting detectors are positioned.

3. The spectral CT apparatus according to claim 1 wherein said at least one source is a single energy source.

4. The spectral CT apparatus according to claim 1 wherein said at least one source is a kV-switching source.

5. The spectral CT apparatus according to claim 1 wherein said at least one source has two or more of said source mounted on said first rotating portion.

6. The spectral CT apparatus according to claim 1 further comprising:
   a predetermined number of integrating detectors placed between adjacent ones of said photon counting detectors.

7. The spectral CT apparatus according to claim 6 wherein said at least one source has at least two of said source.

8. The spectral CT apparatus according to claim 1 wherein said first rotating portion and said second rotating portion have the substantially same center and radius for rotating around the object.

9. The spectral CT apparatus according to claim 1 wherein said second rotating portion is integral with said first rotating portion.

10. The spectral CT apparatus according to claim 1 wherein said detector unit includes any combination of an integrating detector and a photon counting detector.

11. The spectral CT apparatus according to claim 10 wherein said at least one source is a fly focal spot source.

12. The spectral CT apparatus according to claim 1 wherein said photon counting detectors are equidistantly placed at the fixed positions.

13. The spectral CT apparatus according to claim 1 wherein said photon counting detectors are non-equidistantly placed at the fixed positions.

14. The spectral CT apparatus according to claim 1 wherein said at least one source travels along a predetermined helical path with respect to the object.

15. The spectral CT apparatus according to claim 1 wherein said at least one source travels along a predetermined circular path with respect to the object.

16. The spectral CT apparatus according to claim 1 wherein the predetermined path of said at least one source is located outside the predetermined circle on which the said photon counting detectors are positioned.

* * * * *